(12) United States Patent
Yoneda et al.

(10) Patent No.: US 7,498,021 B2
(45) Date of Patent: *Mar. 3, 2009

(54) DENTAL PRODUCTS COMPRISING BONE GROWTH ENHANCING PEPTIDE

(75) Inventors: Toshiyuki Yoneda, San Antonio, TX (US); Motoyoshi Nomizu, Tokyo (JP); Yoshinari Kumagai, Hayward, CA (US); Russell Wayne Blacher, Hayward, CA (US)

(73) Assignee: Acologix, Inc., Hayward, CA (US)

( * ) Notice: Subject to any disclaimer, the term of this patent is extended or adjusted under 35 U.S.C. 154(b) by 198 days.

This patent is subject to a terminal disclaimer.

(21) Appl. No.: 11/379,316

(22) Filed: Apr. 19, 2006

(65) Prior Publication Data
US 2006/0210493 A1 Sep. 21, 2006

Related U.S. Application Data

(63) Continuation of application No. 10/344,046, filed as application No. PCT/US01/25101 on Aug. 9, 2001, now Pat. No. 7,078,021.

(60) Provisional application No. 60/225,879, filed on Aug. 16, 2000.

(51) Int. Cl.
A61K 7/16 (2006.01)
A61K 38/00 (2006.01)
C07K 17/00 (2006.01)

(52) U.S. Cl. .................. 424/49; 424/50; 530/324; 530/326; 530/328; 530/350; 514/2; 514/7; 514/8; 514/12; 514/14; 514/899; 514/901

(58) Field of Classification Search .......... 424/49, 424/50; 530/324, 326, 328, 350; 514/2, 514/7, 8, 12, 14, 899, 901
See application file for complete search history.

(56) References Cited

U.S. PATENT DOCUMENTS

| | | | |
|---|---|---|---|
| 5,015,628 A | 5/1991 | Reynolds | |
| 5,407,664 A | 4/1995 | Konopa | |
| 5,837,674 A | 11/1998 | Kumagai et al. | |
| 5,849,865 A * | 12/1998 | Cheng et al. | 530/317 |
| 6,027,592 A | 2/2000 | Tseng et al. | |
| 6,045,780 A | 4/2000 | Bixler et al. | |
| 6,146,655 A | 11/2000 | Ruben | |
| 6,300,062 B1 | 10/2001 | Cerny et al. | |
| 6,329,357 B1 | 12/2001 | Norman et al. | |
| 6,673,900 B2 | 1/2004 | Rowe | |
| 6,790,639 B2 | 9/2004 | Brown et al. | |
| 6,911,425 B2 | 6/2005 | Kumagai et al. | |
| 7,078,021 B2 * | 7/2006 | Yoneda et al. | 424/49 |
| 7,160,862 B2 * | 1/2007 | Kumagai et al. | 514/12 |
| 2002/0102641 A1 | 8/2002 | Schia Vi et al. | |
| 2003/0166239 A1 | 9/2003 | Brown et al. | |

FOREIGN PATENT DOCUMENTS

| | | |
|---|---|---|
| JP | 4-74132 | 3/1992 |
| JP | 4-506511 | 11/1992 |
| JP | 11-506672 | 6/1999 |
| JP | 11-318498 | 11/1999 |
| JP | 2002-500898 | 1/2002 |
| JP | 2002-512018 | 4/2002 |
| WO | WO 95/14714 | 6/1995 |
| WO | WO 99/08730 | 2/1999 |
| WO | WO 99/43844 | 9/1999 |
| WO | WO 99/48909 | 9/1999 |
| WO | WO 99/60017 | 11/1999 |
| WO | WO 00/52041 | 9/2000 |
| WO | WO 01/72826 | 10/2001 |
| WO | WO 02/05836 | 1/2002 |

OTHER PUBLICATIONS

Abe et al., "Differentiation of mouse myeloid leukemia cells induced by 1α,25-dihydroxyvitamine D3" *PNAS*, 78(8):4990-4994 (1981).
Bairoch et al., "EF-hand motifs in inositol phospholipid-specific phospholipase C" *FEBS*, 269(2:454-456 (1990).
Bikle, "Vitamin D: New Actions, New Analogs, New Therapeutic Potential; Update 1995" *Endocrine Review*, 4(1):77-83 (1995).
Brenza et al., "Parathyroid hormone activation of the 25-hydroxyvitamine D3-1α-Hydroxylase gene promoter" *PNAS* 95:1387-1391 (1998).
Carpenter, "New Persepectives on the Biology and Treatment of X-Linked Hypophsphatemic Rickets" *Pediatric Endocrinology* 44(2):443-465 (1997).
Carswell, "The Potential for Treating Neurodegenerative Disorders with NGF-Inducing Compounds" *Experimental Neurology*, 124:36-42 (1993).

(Continued)

*Primary Examiner*—Jon P Weber
*Assistant Examiner*—Abdel A Mohamed
(74) *Attorney, Agent, or Firm*—Karl Bozicevic; Bozicevic, Field & Francis LLP

(57) ABSTRACT

Dental products such as toothpastes, mouthwash and dental floss are disclosed which products are enhanced by having dissolved, dispersed or coated thereon a compound which promoted bone growth. Preferred compounds are peptide sequences comprising 10 to 50 amino acids are disclosed. The sequences are characterized by containing an integrin binding motif such as RGD sequence and the remainder of amino acids contiguous with the RGD sequence in matrix extracellular phosphoglycoprotein. The sequences may be formulated for dispersed in toothpaste or a mouthwash and administered to enhance bone/tooth growth. When the dental products are used repeatedly over time they enhance good dental health.

3 Claims, 4 Drawing Sheets

OTHER PUBLICATIONS

Chappard et al., "Effects of Tiludronate on Bone Loss in Paraplegic Patients" *Journal of Bone Mineral Research*, 10(1):112-118 (1995).

Chauvaux et al., "Calcium-binding affinity and calcium-enhanced activity of *Clostridium thermocellum* endoglucanase D" *Biochem J.*, 265:261-265 (1990).

Davis, "The Many Faces of Epidermal Growth Factor Repeats" *The New Biologist*, 2(5):410-419 (1990).

Ecarot et al., "Defective Bone Formation by Hyp Mouse Bone Cells Transplanted into Normal Mice: Evidence in Favor of an Intrinsic Osteoblast Defect" *Journal of Bone and Mineral Research*, 7:215-200 (1992).

Ecarot et al., "Effect of 1,25-Dihydroxyvitamin D3 Treatment on Bone Formation by Transplanted Cells from Normal and X-Linked Hypophosphatemic Mice" *Journal of Bone and Mineral Research*, 10:424-431 (1995).

Economou et al., "The Rhizoblum nodulation gene nodO encodes a CA2+-binding protein that is exported without N-terminal cleavage and is homologous to haemolysin and related proteins" *The EMBO Journal*, 9(2):349-354 (1990).

Eto et al., "Assay of 25-Hydroxyvitamin D3 1 α-Hydroxylase in Rat Kidney Mitochondria" *Analytical Biochemistry*, 258:53-58 (1998).

Ferris et al., "RGD-coated titanium implants stimulate increased bone formation in vivo" *Biomaterials*, 20:2323-2331 (1999).

Fratzl et al., "Abnormal Bone Mineralization After Fluoride Treatment in Osteoporosis: A Small-Angle X-ray Scattering Study" *Journal of Bone and Mineral Research* 9(10):1541-1549 (1994).

Gennari et al., "Management of Osteoporosis and Paget's Disease" *Drug Safety*, 11(3):179-195 (1994).

Hewison et al., "1α-Hydroxylase and the action of vitamin D" *Journal of Molecular Endocrinology*, 25:141-148 (2000).

Hilfiker et al., "Characterization of a murine type II sodium-phosphate cotransporter expressed in mammalian small intestine" *PNAS*, 95:14564-14569 (1998).

Inomata et al., "Effect of 1α(OH)-vitamin D3 on insulin secretion in diabetes melitus" *Bone and Mineral*, 1:187-192 (1986).

Kato et al., "Molecular Genetics of Vitamin D-Dependent Hereditary Rickets" *Hormone Research*, 57:73-78 (2002).

Kawasaki et al., "Calcium-Binding Proteins 1: EF Hands" *Protein Profile*, 2(4):305-356 (1995).

Kimmel-Jehan et al., "Cloning of the mouse 25-hydroxyvitamin D3-1α-hydroxylase (CYP1α) gene" *Biochimica et Biophysica Acta*, 1475:109-113 (2000).

Lajeunesse et al., "Direct demonstration of a humorally-mediated inhibition of renal phosphate transport in the Hyp mouse" *Kidney International* 50:1531-1538 (1996).

Lopez-Moratalla et al., "A common structural motif in immunopotentiating peptides with sequences present in human autoantigens. Elicitation of a response mediated by monocytes and Th1 cells" *Biochimica et Biophysica Acta*, 1317:183-191 (1996).

Lufkin et al., "Pamidronate: An Unrecognized Problem in Gastrointestinal Tolerability" *Osteoporosis Int.* 4:320-322 (1994).

Martin et al., "Strategies to Minimize Bone Disease in Renal Failure" *American Journal of Kidney Diseases*, 38(6):1430-1436 (2001).

Meyer et al., "The Renal Phosphate Transport Defect in Normal Mice Parabiosed to X-Linked Hypophosphatemic Mice Persists After Parathyroidectomy" *Journal of Bone and Mineral Research*, 4(4):523-532 (1989).

Meyer et al., "Parabiosis Suggests a Humoral Factor Is Involved in X-Linked Hypophsphatemia in Mice" *Journal of Bone and Mineral Research*, 4(4):493-500 (1989).

Miller et al., "Genetics of vitamin D biosynthesis and its disorders" *Best Practice & Research Clinical Endocrinology and Metabolism*, 15(1):95-109 (2001).

Moncrief et al., "Evolution of EF-Hand Calcium-Modulated Proteins. I. Relationships Based on Amino Acid Sequences" *J. Mol. Evol.*, 30:522-562 (1990).

Morgan et al., "Renal Transplantation in Hypophsphatemia With Vitamin D-Resistant Rickets" *Arch. Intern. Med.*, 134:549-552 (1974).

Muller et al., "1α,25-Dihydroxyvitamin D3 and a novel vitamin D analogue MC 903 are potent inhibitors of human interleukin 1 in vitro" *Immunology Letters*, 17:361-366 (1988).

Mundy et al., "Stimulation of Bone Formation in Vitro and in Rodents by Statins" *Science*, 286:1946-1949 (1999).

Nesbitt et al., "Crosstransplantation of Kidneys in Normal and Hyp Mice" *J. Clin. Invest.* 89:1453-1459 (1992).

Nesbitt et al., "Phosphate Transport in Immortalized Cell Cultures from the Renal Proximal Tubule of Normal and Hyp Mice: Evidence That the HYP Gene Locus Product Is an Extrarenal Factor" *Journal of Bone and Mineral Research*, 10(9):1327-1333 (1995).

Nesbitt et al., "Normal Phosphate Transport in Cells from the S2 and S3 Segments of *Hyp*-Mouse Proximal Renal Tubules" *Endocrinology*, 137(3):943-948 (1996).

Nesbitt et al., "Abnormal Parathyroid Hormone-Realted Peptide Formulation of Renal 25-Hydroxyvitamin D-1-Hydroxylase in Hyp Mice: Evidence for a Generalized Defect of Enzyme Activity in the Proximal Convoluted Tubule" *Endocrinology*, 127(2) :843-848 (1990).

Peterson et al., "Identification of Osteoblast/Osteocyte Factor 45 (OF45), a Bone-specific cDNA Encoding and RGD-containing Protein That Is Highly Expressed in Osteoblasts and Osteocytes" *The Journal of Biological Chemistry*, 275(46):36172-36180 (2000).

Qiu et al., "Parental origin of mutant allele does not explain absence of gene dose in X-linked *Hyp* mice" *Gene Res. Camb.*, 62:39-43 (1993).

Rowe et al., "Distribution of mutations in the PEX gene in families with X-linked hypophosphataemic rickets (HYP)" *Human Molecular Genetics* 6(4):539-549 (1997).

Rowe, "The role of the PHEX gene (PEX) in families with X-linkd hypophosphataemic rickets" *Mineral Metabolism*, 367-376 (1998).

Rowe et al., "Candidate 56 and 58 kDa Protein(s) Responsible for Mediating the Renal Defects in Oncogenic Hypophosphatemic Osteomalacia" *Bone*, 18(2):159-169 (1996).

Schafer et al., "Isolation of YAC Clone Covering a Cluster of Nine S100 Genes of Human Chromosome 1q21: Rationale for a New Nomenclature of the S100 Calcium-Binding Protein Family" *Genomics*, 25:638-643 (1995).

Schneider et al., "Does HRT Modify Risk of Gynecological Cancers?" *Int. J. Fertil.*, 40(Supp. 1):40-53 (1995).

Springer et al., "A Novel Ca2+ Binding β Hairpin Loop Better Resembles Integrin Sequence Motifs Than the EF Hand" *Cell*, 102:275-277 (2000).

Takeyama et al., "25-Hydroxyvitamin D3 1α-Hydroxylase and Vitamin D Synthesis" *Science*, 277:1827-1830 (1997).

Traianedes et al., "5-Lipoxygenase Metabolites Inhibit Bone Formation" *Endocrinology*, 139(7):3178-3184 (1998).

Yang et al., "Peptide analogs from E-cadherin with different calcium-binding affinities" *J. Peptide Res.*, 55:203-215 (2000).

Yoshida et al., "Identification of a Renal Proximal Tubular Cell-Specific Enhancer in the Mouse 25-Hydroxyvitamin D 1α-Hydroxylase Gene" *J. Am. Soc. Nephrol.*, 13:1455-1463 (2002).

Yoshida et al., "Mediation of Unusually High Concentrations on 1,25-Dihydroxyvitamin D in Homozygous *klotho* Mutant Mice by Increased Expression of Renal 1α-Hydroxylase Gene" *Endocrinology*, 143(2):683-689 (2002).

Zehnder et al., "Extrarenal Expression of 25-Hydroxyvitamin $D_3$-1α-Hydroxylase" *The Journal of Clinical Endocrinology & Metabolism*, 86(2):888-894 (2001).

Zoidis et al., "Phex cDNA cloning from rat bone and studies on Phex mRNA expression: tissue-specificity, age-dependency, and regulation by insulin-like growth factor (IGF) I in vivo" *Molecular and Cellular Endocrinology*, 168:41-51 (2000).

Fisher et al., "Inhibition of osteoclastic bone resorption in vivo by echistatin an—arginyl-clycyl-aspartyl- (RGD)-containing protein" *Endocrinology*, 132(3):1411-1413 ((1993).

George et al., "Characterization of a Novel Dentin Matrix Acidic Phosphorprotein" *J. Biol. Chem.* 268(17):12624-12630 (1993).

Gronowicz et al., "Synthetic Peptide Containing Arg-Gly-Asp Inhibits Bone Formation and Resorption in a Mineralizing Organ Culture System of Fetal Rat Parietal Bones" *J. Bone and Mineral Res.* 9(2):193-201 (1994).

Hayashibara et al., "A Synthetic Peptide Fragment of Human MEPE Stimulates New Bone Formation In Vitro and In Vivo" *Journal of Bone and Mineral Resesarch* 19(3):455-462 (2004).

Horton et al., "Arg-Gly-Asp (RGD) Peptides and the Anti-Vitronectin Receptor Antibody 23C6 Inhibit Dentine Resorption and Cell Spreading by Osteoclasts" *Experimental Cell Research* 915:368-375 (1991).

Rowe et al., "MEPE, a New Gene Expressed in Bone Marrow and Tumors Causing Osteomalacia" *Genomics* 67:54-68 (2000).

Rowe "The PEX Gene: Its Role in X-Linked Rickets., Osteomalacia, and Bone Mineral Metabolism" *Experimental Nephrology* 5:355-363 (1997).

Stubbs et al., "Characterization of Native and Recombinant Bone Sialoprotein: Delineation of the Mineral-Binding and Cell Adhesion Domains and Structural Analysis of the RGD Domain" *J. Bone and Mineral Res.* 12(8):1210-1222 (1997).

* cited by examiner

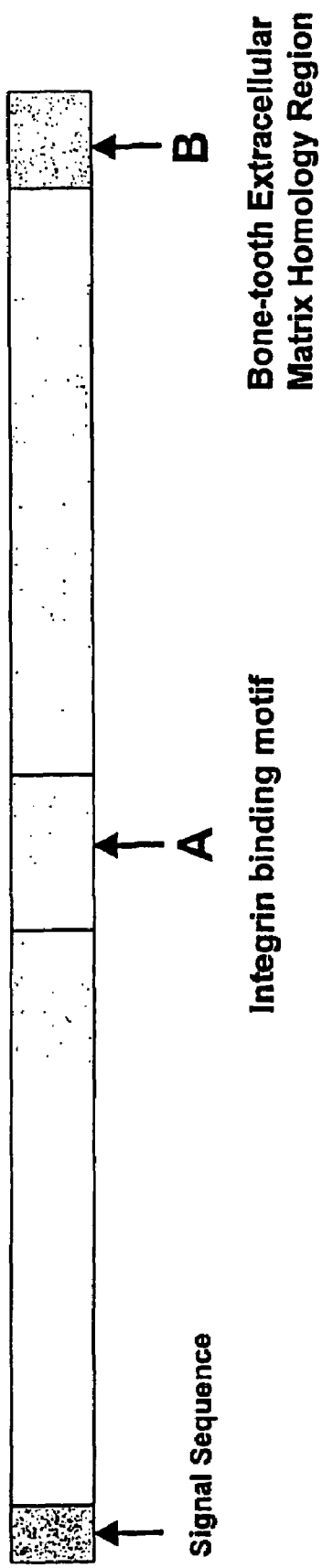
Figure 2. Structure of Matrix Extracellular Phosphoglycoprotein

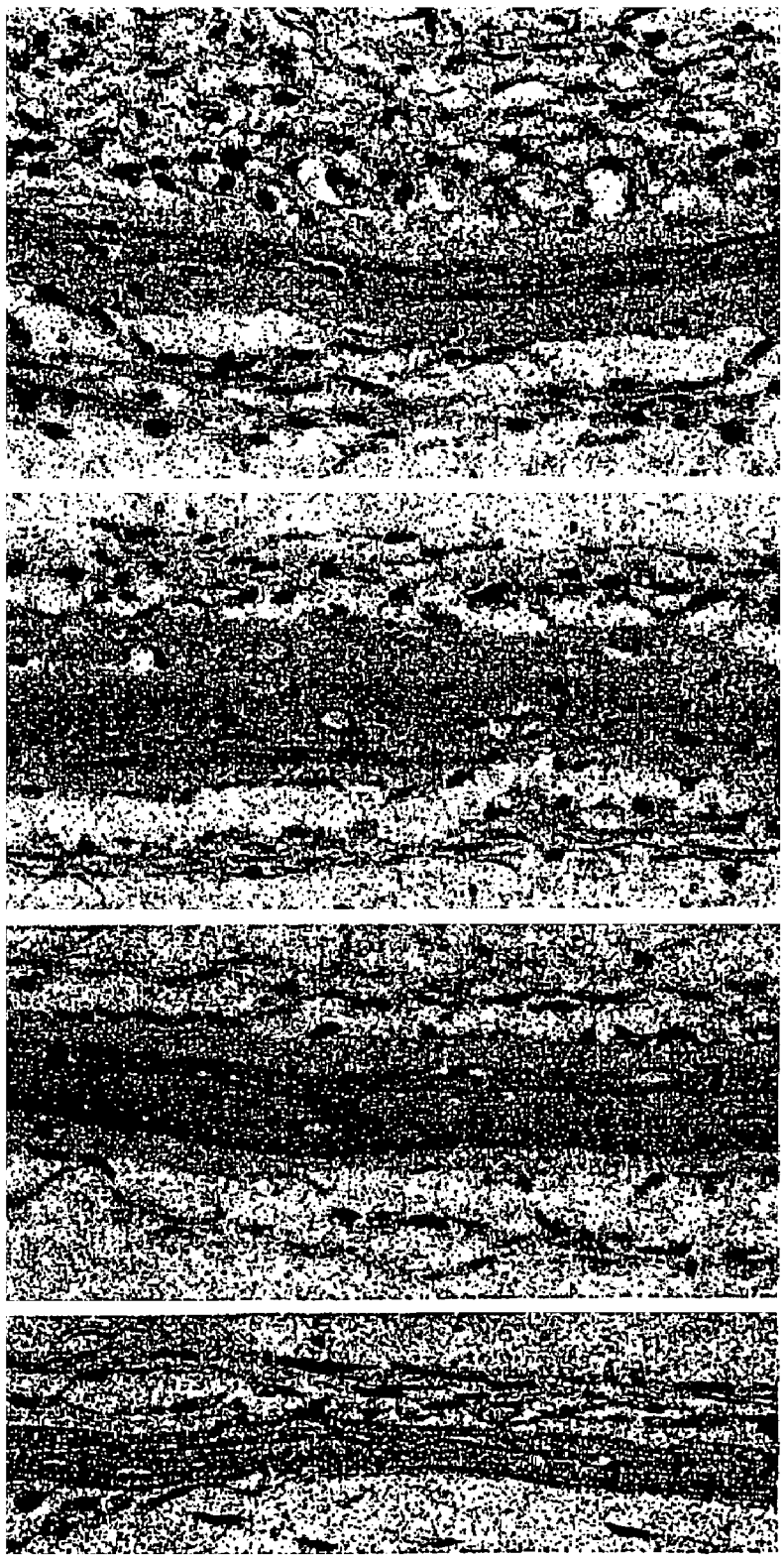
Figure 3. Bone Formation and Osteoblast Increase

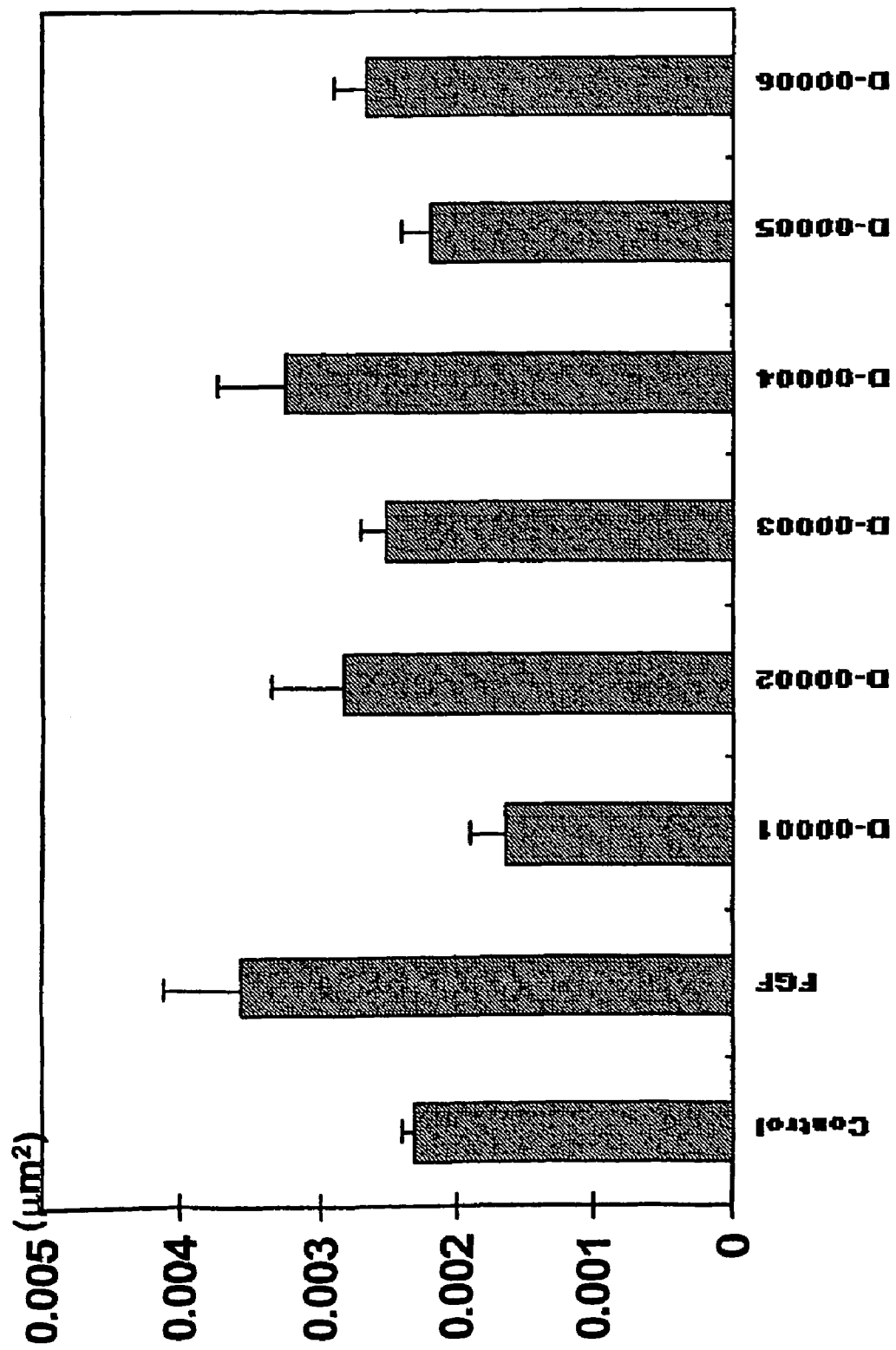
Figure 4. New Bone Area in Mouse Calvaria Assay

DENTAL PRODUCTS COMPRISING BONE GROWTH ENHANCING PEPTIDE

This application is a continuation of application of Ser. No. 10/344,046, filed Feb. 7, 2003 (now U.S. Pat. No. 7,078,021 issued Jul. 18, 2006), which is a 371 National Phase of International Patent Application Serial No. PCT/US01/25101, filed Aug. 9, 2001 which claims priority to U.S. Provisional Patent Application Ser. No. 60/225,879, filed Aug. 16, 2000 which are incorporated herein by reference in their entirety noting that the current application controls to the extent there is any contradiction with any earlier application and to which applications we claim priority under 35 USC §120 and §119.

TECHNICAL FIELD

The invention relates generally to the field of dental products and more particularly to such products supplemented so that they are useful in treating skeletal diseases.

BACKGROUND OF THE INVENTION

A wide range of dental products including toothpastes, mouthwashes and dental floss are used. These products are generally intended to reduce dental diseases. However, it is well-documented that disorders of skeletal tissues and mineral metabolism cause numerous significant health problems and such can be specific to dental problems.

In humans, the maximum bone mass occurs between the age of 15 and 40 and is referred to as "peak bone mass." After such peak bone mass age, bone mass begins declining gradually and the mechanical strength of the bone is accordingly reduced. Consequently, when mechanical strength declines to a certain level, the individual is at greater risk of bone fracture. This natural occurrence is called osteoporosis if severe enough to be pathogenic.

The speed at which bone loss occurs differs among individuals, and especially with respect to gender. In females, the speed of bone loss accelerates immediately after menopause (See FIG. 1) because of a significant decline in available estrogen, a hormone which plays a critical role in maintaining healthy bone metabolism. Postmenopausal osteoporosis constitutes an important clinical problem because it afflicts significant numbers of women. Notably, the ratio of female to male osteoporosis patients is 3:1.

The majority of bone diseases are characterized by loss of bone minerals, weakening of bones and consequently, an increase of the frequency and severity of bone fractures, which are called "pathological fracture." In the elderly population, this has significant social ramifications as well, as many of those with bone fractures have difficulty with mobility, which often leads to the deterioration of other mental and physical functions, resulting in dementia, muscular weakness and/or fatigue. In addition, morbidity and pain are significantly increased by thrombotic events, such as pulmonary embolism which occur as a result of hip or pelvic fractures.

In the United States alone, it is said that 52 million women over age of 45 will suffer from osteoporosis by 2000. Current worldwide osteoporosis population is around 200 million. Annual incidence of pathological fracture in the United States alone is approximately 1.5 million. It is estimated that annual medical costs for those osteoporosis patients in the United States and world are $14 billion and $60 billion, respectively.

Renal failure is also a significant health problem related to mineral metabolism and skeletal formation, and the number of its patients is increasing rapidly. Renal function is declining gradually over several to ten years period in these patients. When the renal function becomes approximately a quarter ($\frac{1}{4}$) of the healthy level, the patients are classified to chronic renal failure. When it becomes approximately one sixth ($\frac{1}{6}$) thereof, they need to start dialysis and are called end stage renal disease (ESRD). In patients with chronic renal failure, serum levels of important minerals such as calcium and phosphate lose their normal homeostasis, which results in malformation of skeleton. It is called renal osteodystropny (ROD), which is a secondary osteoporosis from renal failure. ROD can also cause pathological fracture like osteoporosis. The prevalence of end stage renal disease (ESRD) in the United States is rapidly increasing and about to reach 300 thousand in 2000. As ESRD is a part of chronic renal failure, there should be much higher number of ROD patients.

There are several other diseases of skeletal tissues and mineral metabolism such as Paget's Disease, rikets, osteopetrosis, hyperparathyroidism, and so forth and number of patients are affected by these diseases.

Metabolically, bone is a highly active organ with bone resorption and formation occurring continuously (remodeling). Bone resorption is facilitated by osteoclasts which are differentiated from monocyte/macrophage lineage cells. Osteoclasts adhere to the surface of bone and degrade bone tissue by secreting acids and enzymes. Osteoblasts facilitate bone formation by adhering to degraded bone tissue and secreting bone matrix proteins, which are mineralized mostly by calcium and phosphate. Osteoblasts differentiate into bone cells (osteocytes), and become a part of bone tissue.

Numerous experimental approaches have been attempted to either accelerate bone formation or diminish bone resorption. For example, growth factors such as BMPs (bone morphogenetic proteins), TGFβ (transforming growth factor β), IGF (insulin-like growth factor), fibroblast growth factor (FGF) are known to have potent biological activities in bone formation. In particular, a few subfamily molecules of BMP such as BMP-2 are regarded one of the most potent growth factors for hard tissue. However, these factors have not been developed as therapeutic agents for systemic bone diseases. It is because none of them can be delivered to the bone selectively and some of these factors such as BMPs convert soft tissue into hard tissue. It is called ectopic calcification and a critical adverse effect for them when they are used systemically. Further, the processes of bone formation and resorption are so closely connected and that makes selective increase of bone formation or selective inhibition of bone resorption extremely difficult.

Currently, there is a need for an effective treatment for bone loss. Therapeutic agents such as estrogen, calcitonin, vitamin D, fluoride, Iprifravon, bisphosphonates, and a few others have failed to provide a satisfactory means of treatment. (Gennari et al., *Drug Saf.* (1994) 11(3):179-95).

Estrogen and its analogues are frequently administered to patients with postmenopausal osteoporosis. Estrogen replacement therapy involves administration of estrogen just prior to or after the onset of menopause. However, as is often the case with steroid hormones, the long term use of estrogen has significant adverse effects such as breast and other gynecological cancers (Schneider et al., *Int. J. Fertil. Menopausal Study* (1995) 40(1):40-53).

Calcitonin, an endogenous hormone produced by the thyroid, binds selectively to osteoclasts, via its receptor, and inactivates them. Since the osteoclast is the only cell which can dissolve bone tissue, calcitonin binding can block or slow down bone degradation caused by the osteoclast. However, this biological mechanism is very short-lived, as the osteoclasts become tolerant to this drug relatively quickly. Therefore, the use of calcitonin does not provide an effective therapeutic option.

Fluoride has been shown to increase bone mass when it is administered to humans. However, while bone mass is increased, mechanical strength is not. Therefore, despite the increase in apparent bone mass, the risk of fracture remains (Fratzl et al., *J. Bone Mineral Res.* (1994) 9(10):1541-1549). In addition, fluoride administration has significant health risks.

Iprifravon has been used to treat osteoporosis in limited areas in the world. However, the actual efficacy of this compound is questionable and it is not widely accepted as a useful therapeutic agent for bone diseases.

Bisphosphonates are compounds derivatized from pyrophosphate. Synthesis involves replacing an oxygen atom situated between two phosphorus atoms with carbon and modifying the carbon with various substituents. While bisphosphonates are known to suppress bone resorption, they have little effect on bone formation. Furthermore, bisphosphonates adhere to the bone surface and remain there for very long time causing a long-term decrease in bone tissue turnover. As bone tissue needs to be turned over continuously, this decrease in turnover ultimately results in bone deterioration (Lufkin et al., *Osteoporos. Int.* (1994) 4(6):320-322; Chapparel et al., *J. Bone Miner. Res.* (1995) 10(1):112-118).

Another significant problem with the agents described above is that with the exception of fluoride and iprifravon, they are unsuitable for oral administration, and thus, must be given parenterally. Since bone disorders are often chronic and require long-term therapy, it is important that therapeutic agents be suitable for oral administration.

In summary, a significant need exists for a therapeutic agent which can prevent or treat bone loss. In particular, a new drug that can selectively increase bone formation and/or number of osteoblast without affecting bone resorption or soft tissue is highly desired.

Another major health problem relating to skeleton and mineral metabolism is that with teeth. In the United States alone, it is estimated that 67 million people are affected by periodontal disease and that the annual cost of its treatment is approximately $6.0 billion in 2000. It is said 90% of the entire population experience dental caries in their lives. The annual cost to treat them is over $50 billion per year in the United States alone.

Dental caries is a universal disease and affects children and adults. Periodontal disease, on the other hand, affects mostly adults, and in particular, the aged. In many cases, the patient's gum is inflamed and destroyed, the alveolar bone that supports the teeth is deteriorated. Cement that composes the core of the root is also damaged, and subsequently, teeth fall out. One of the most common treatments for tooth loss involves the use of a dental implant. An artificial implant (osseointegrated dental implants) is placed in the space where the tooth was lost. In severe cases, an entire denture is replaced by implants. However, implants frequently loosen, or fall out because their fixation on the alveolar bone is not always successful. Since alveolar bone is somehow damaged in these patients, the implant can not always be supported well by alveolar bone. When alveolar bone is severely damaged, autogenous bone grafting is made. In this case, a bone graft taken from another skeletal tissue of the same patient is grafted in the damaged alveolar area so that the hard tissue is regenerated and sinus is elevated there. Since these treatments require expensive bio-compatible materials and/or highly skilled techniques, the cost of treatment is usually very high.

It is believed that dental caries is caused by acidic condition in the oral cavity. For instance, sugars are converted to acid and dissolve the surface of the teeth. Although only enamel and a part of dentin is affected in many cases, the damage can reach the pulp cavity in severe cases that cause significant pain. The most typical treatment is filling the caries lesion with undegradable materials such as metals or metal oxide. Treatment of dental caries mostly depends upon those materials and the techniques by the dentists, which is often expensive.

Although a few therapeutic agents have been developed and used in dental area, they are generally only anti-inflammatory drugs, analgesics, and antibiotics. No generally effective therapeutic agent that directly improves periodontal hard tissues has been developed. Obviously, there is a significant demand for a therapeutic agent that promotes regeneration of alveolar bone and/or teeth, and increases the number and activity of odontoblasts/osteoblasts that help form of dental tissues.

SUMMARY OF THE INVENTION

Dental products including toothpaste, mouthwash, and dental floss are disclosed which products are comprised of a compound which enhance bone growth. The compound is any of a class of compounds which are useful in treating or preventing a condition associated with skeletal loss or weakness. The compounds are peptides or analogs thereof which comprise between 10 and 50 monomer (e.g. amino acids) units. The amino acid sequence comprises an integrin binding motif sequence which may be in the D- or L-conformation. The remaining monomer units (the sequence other than the integrin binding motif) in the compound may be amino acid analogs but are preferably naturally occurring amino acids having a sequence which is substantially the same as an amino acid sequence contiguous with the RGD sequence in the naturally occurring protein, matrix extracellular phosphoglycoprotein (Rowe et. al., *Genomics* (2000) 67:56-68).

An aspect of the invention is a set of peptides and/or peptide analogs.

Another aspect of the invention is to provide toothpaste which comprises a sufficient concentration of a compound of the invention to enhance tooth and/or alveolar bone growth on areas where deterioration has occurred.

Yet another aspect of the invention is to provide a mouthwash which comprises a sufficient concentration of a compound of the invention to enhance tooth and/or alveolar bone growth on areas where deterioration has occurred.

Still another aspect of the invention is a dental floss having coated thereon and/or embedded therein a compound of the invention in an amount such that repeated application to teeth and/or alveolar bone results in enhanced tooth and/or alveolar bone growth on areas where deterioration has occurred.

A feature of the invention is that a compound of the invention comprised an integrin binding motif sequence in a D or L conformation.

An advantage of the invention is that a compound of the invention enhances skeletal growth.

Another advantage of the invention is that a compound of the invention enhances the amount of osteoblast and possibly odontoblast cells on the surface of new skeletal growth.

Another aspect of the invention is to provide a formulation for therapeutic use which comprises a sufficient concentration of a compound of the invention and can be injected into the pulp of teeth, the space between the root of teeth and gum, or alveolar bone to prevent the damage on teeth and/or alveolar bone or regenerate the hard tissue in the damaged teeth and/or alveolar bone.

An object of the invention is to provide a method of treating skeletal loss by the administration/application of any formulation/composition of the invention.

These and other objects, aspects, features and advantages will become apparent to those skilled in the art upon reading this disclosure.

BRIEF DESCRIPTION OF THE FIGURES

FIG. 2 is a schematic drawing of a matrix extracellular phosphoglycoprotein wherein the area designated as "A" includes sequences which match peptides of the present invention and the area designated as "B" is a highly homologous motif to a group of bone-tooth matrix phosphoglycoproteins such as osteopontin (OPN), dentin sialophosphoprotein (DSPP), dentin matrix protein 1 (DMP1), and bone sialoprotein II (IBSP).

FIGS. 3A, 3B, 3C, and 3D are actual photographs of bone cross-sections (from a seven day mouse calvaria organ culture study) showing the effects of a control (FIG. 3A), fibroblast growth factor-1 (FGF-1) (FIG. 3B), and two peptides of the invention designated D-00004 and D-00006 (FIGS. 3C and 3D, respectively).

FIG. 4 is a graph comparing the effects of different compounds on calvaria.

DETAILED DESCRIPTION OF THE PREFERRED EMBODIMENTS

Figure 1:
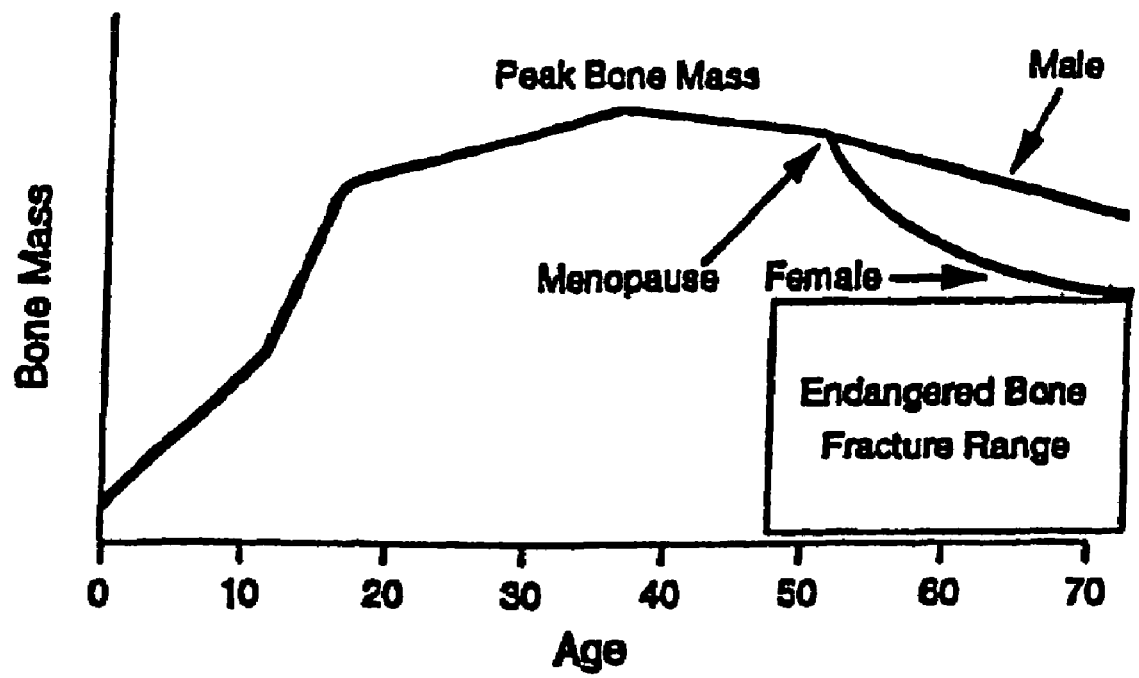
FIG. 1 is a graph showing the relationship between bone mass and age in humans.

Before the toothpastes, mouthwashes, dental floss products, peptides, analogs, formulations, and methodology of the present invention are described, it is to be understood that this invention is not limited to any particular embodiment described, as such may, of course, vary. It is also to be understood that the terminology used herein is with the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a peptide" includes a plurality of such peptides and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "dental product" refers to all and any product used in the mouth. Preferably the product is used on a regular basis by consumers such as toothpaste, mouthwash and dental floss. However, the term includes products used solely by oral surgeons and dentists such as dental implants and materials used to fill dental cavities.

The terms "treat", "treating", "treatment" and the like are used interchangeably herein and mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed the disease such as enhancing the effect of vitamin D. "Treating" as used herein covers treating a disease in a vertebrate and particularly a mammal and most particularly a human, and includes:

(a) preventing the disease from occurring in a subject which may be predisposed to the disease but has not yet been diagnosed as having it;

(b) inhibiting the disease, i.e. arresting its development; or (c) relieving the disease, i.e. causing regression of the disease.

The invention is particularly directed towards peptides which make it possible to treat patient's which have experienced bone loss or which would be expected to experience bone loss and thus is particularly directed towards preventing, inhibiting or relieving the effects of bone loss. A subject is "treated" provided the subject experiences a therapeutically detectable and beneficial effect which may be measured based on a variety of different criteria including increased bone growth, increased bone strength or other characteristics generally understood by those skilled in the art to be desirable with respect to the treatment of diseases related to bone.

The term "antibody" is meant an immunoglobulin protein capable of binding an antigen. The term "antibody" as used herein is intended to include antibody fragments (e.g. F(ab')$_2$, Fab', and Fab) capable of binding an antigen or antigenic fragment of interest.

The term "binds specifically" is meant high avidity and/or high affinity binding of an antibody to a specific peptide—specifically a peptide of the invention. Antibody binding to its specific target epitope is stronger than the binding of the antibody to other epitopes on the peptide or to other epitopes on other peptides. Antibodies which bind specifically to a peptide of interest may be capable of binding to other peptides at a weak, yet detectable level (e.g. 10% or less of the binding shown to the peptide of interest). Such weak binding or background binding, is readily discernable from the specific antibody binding to the peptide of interest, e.g. by the use of appropriate controls.

The term "skeletal loss" refers to any situation in which skeletal mass, substance or matrix or any component of the skeleton, such as calcium and phosphate, is decreased or the bone is weakened such as in terms of its ability to resist being broken.

The term "skeleton" includes both bone and teeth. In the same manner, the term "skeletal" means both bone and teeth.

The term "osteoporosis" is intended to refer to any condition involving bone loss, i.e. involving a reduction in the amount of bone mass or substance resulting from any cause. The term particularly results in a bone loss resulting from demineralization of the bone, post menopausal or peri-menopausal estrogen decrease or nerve damage.

The term "subject" refers to any vertebrate, particularly any mammal and most particularly including human subjects.

Invention in General

In general the invention comprises any dental product comprising a compound which enhances bone growth. The product is preferably a toothpaste, mouthwash or dental floss. The compound is preferably a peptide comprising from 10 to 50 amino acids. The amino acids are preferably one of the twenty naturally occurring L-amino acids. However, D-amino acids may be present as may amino acid analogs. A sequence of the invention will comprise an integrin binding motif such as RGD sequence in either the L- or D-form but preferably in the L-conformation. The peptide of the invention can be amidated or non-amidated on its C-terminus, or carboxylated or non-carboxylated on its N-terminus. The peptide of the invention may or may not contain a glycosaminoglycan binding motif such as SGDG sequence in L- or D-isomer form. A compound of the invention is still further characterized by biological activity i.e. it enhances skeletal growth as well as the growth or recruiting of osteoblast or odontoblast cells on surface of the new skeletal growth.

Specific Dental Products

The present invention is broadly applicable to all types of dental products and is particularly useful in connection with products used by consumers on a regular basis such as toothpaste, mouthwash and dental floss.

Specific examples of toothpastes which could be modified by having a compound of the invention dissolved, suspended or mixed therein include those toothpaste compositions disclosed and described in U.S. Pat. Nos. 6,045,780; 5,951,966; 5,932,193; 5,932,191; and 5,876,701. These patents as well as the patents and publications cited in these patents are incorporated herein by reference for the purpose of disclosing and describing various toothpaste compositions which can be used in connection with the present invention.

Compounds of the invention can also be used in combination with all types of mouthwashes. The various compounds including specific peptides disclosed herein can be dissolved or dispersed within a wide range of different compositions including the mouthwash compositions disclosed and described within U.S. Pat. Nos. 5,993,785; 5,817,295; 5,723,106; 5,707,610; 5,549,885; 5,470,561; 5,466,437; 5,455,023; 5,407,664; 5,328,682; and 5,256,401 all of which are incorporated herein by reference along with the patents and publications cited therein in order to disclose and describe various mouthwash compositions useful in connection with the present invention.

Compounds of the invention can also be coated on or absorbed into various types of filament materials used as dental flosses. Specific examples of dental floss materials which can be used in combination with the present invention include those disclosed and described within U.S. Pat. Nos. 6,102,050; 6,080,481; 6,027,592; 6,026,829; 6,016,816; 5,967,155; 5,937,874; 5,915,392; 5,904,152; 5,875,797; and 5,845,652 all of which are incorporated herein by reference along with the patents and publications cited therein in order to disclose and describe dental floss filament materials which can be used in combination with the present invention.

Specific Peptides

Specific examples of peptides of the invention comprise seven to forty-seven amino acids on either side of the RGD sequence of the naturally occurring sequence of matrix extracellular phosphoglycoprotein. Thus, examples of peptides of the invention comprising sequences taken from the following sequence and including the RGD sequence shown in bold:

(SEQ ID NO: 1)
DSQAQKSPVKSKSTHRIQHNIDYLKHLSKVKKIPSDFEGSGYTDLQERGD

NDISPFSGDGQPFKDIPGKGEATGPDLEGKDIQTGFAGPSEAESTHL

Specific examples of peptides of the invention which comprise the RGD sequence as the terminal sequence include the following:

| | |
|---|---|
| AQKSPVKSKSTHRIQHNIDYLKHLSKVKKIPSDFEGSGYTDLQERGD | (SEQ ID NO:2) |
| RGDAQKSPVKSKSTHRIQHNIDYLKHLSKVKKIPSDFEGSGYTDLQE | (SEQ ID NO:3) |
| DSQAQKSPVKSKSTHRIQHNIDYLKHLSKVKKIPSDFEGSGYTDRGD | (SEQ ID NO:4) |
| RGDSPVKSKSTHRIQHNIDYLKHLSKVKKIPSDFEGSGYTDLQE | (SEQ ID NO:5) |
| DSQAQKSPVKSKSTHRIQHNIDYLKHLSKVKKIPSDFEGSGRGD | (SEQ ID NO:6) |
| RGDTHRIQHNIDYLKHLSKVKKIPSDFEGSGYTDLQE | (SEQ ID NO:7) |
| DSQAQKSPVKSKSTHRIQHNIDYLKHLSKVKKIPSDFERGD | (SEQ ID NO:8) |
| RGDLKHLSKVKKIPSDFEGSGYTDLQE | (SEQ ID NO:9) |
| DSQAQKSPVKSKSTHRIQHNIDYLKHLSKVKKIPSRGD | (SEQ ID NO:10) |
| RGDLSKVKKIPSDFEGSGYTDLQE | (SEQ ID NO:11) |

-continued

```
DSQAQKSPVKSKSTHRIQHNIDYLKHLSKRGD                (SEQ ID NO:12)

RGDVKKIPSDFEGSGYTDLQE                           (SEQ ID NO:13)

DSQAQKSPVKSKSTHRIQHNIDYLKRGD                    (SEQ ID NO:14)

RGDIPSDFEGSGYTDLQE                              (SEQ ID NO:15)

DSQAQKSPVKSKSTHRIQHNIDRGD                       (SEQ ID NO:16)

RGDDFEGSGYTDLQE                                 (SEQ ID NO:17)

DSQAQKSPVKSKSTHRRGD                             (SEQ ID NO:18)

RGDGSGYTDLQE                                    (SEQ ID NO:19)

DSQAQKSPVKRGD                                   (SEQ ID NO:20)

RGDGYTDLQE                                      (SEQ ID NO:21)

DSQAQKSRGD                                      (SEQ ID NO:22)

RGDNDISPFSGDGQPFKDIPGKGEATGPDLEGKDIQTGFA        (SEQ ID NO:23)
```

Specific examples of the peptides of the invention which comprise the RGD internally include the following:

```
NDI RGDSPFSGDGQPFKDIPGKGEATGPDLEGKDIQTGFA       (SEQ ID NO:24)

NDISPF RGDSGDGQPFKDIPGKGEATGPDLEGKDI            (SEQ ID NO:25)

NDISPFSGD RGDGQPFKDIPGKGEATGPDL                 (SEQ ID NO:26)

FSGDGQPFKDIPGKGEATGPDLEGKDIQTGFAGPSEAES RGDTHL  (SEQ ID NO:27)

IPGKGEATGPDLEGKDIQTGFAGPSE RGDAESTHL            (SEQ ID NO:28)

EATGPDLEGKDIQTGFAG RGDPSEAESTHL                 (SEQ ID NO:29)

NDISPFSGDGQPFKD RGDIPGKGEATGPDLEGK              (SEQ ID NO:30)

GKGEATGPDLEGKDI RGDQTGFAGPSEAESTHL              (SEQ ID NO:31)

FSGDGQPFKDIPGKGEATG RGDPDLEGKDIQTGFAGPSEA       (SEQ ID NQ:32)

DGQPFKDIPGKGEATG RGDPDLEGKDIQTGF                (SEQ ID NO:33)

PFKDIPGKGEATG RGDPDLEGKDIQ                      (SEQ ID NO:34)

DIPGKGEATG RGDPDLEGKDIQTGFAGP                   (SEQ ID NO:35)

DGQPFKDIPGKGEATG RGDPDLEGKDIQTGF                (SEQ ID NO:36)

GKGEATG RGDPDLEGKDIQTGFAGPSEA                   (SEQ ID NO:37)

EATG RGDPDLEGKDIQTGF                            (SEQ ID NO:38)

EATG RGDPDLEGK                                  (SEQ ID NO:39)

EATG RGDPDL                                     (SEQ ID NO:40)
```

All or any of the amino acids in the above sequences may be in the D- or L-conformation and may be substituted with equivalent analogs. The preferred embodiments comprise naturally occurring amino acids in the L-conformation.

All or any of the above sequences may be amidated or no-amidated on their C-terminus, or carboxylated or non-carboxylated on their N-terminus.

Matrix extracellular phosphoglycoprotein was cloned and characterized from a human tumor that caused osteomalacia in the patients. This extremely rare type of tumor called Oncogenic Hypophosphatemic Osteomalacia (OHO) tumor has been known to cause renal phosphate leak, hypophosphatemia (low serum phosphate levels), low serum calcitriol (1,25-vitamin D3), and abnormalities in skeletal mineralization (Osteomalacia). In the patients of OHO tumor, resection of the tumors results in remission of all of the above symptoms and it has been proposed that a circulating phosphaturic factor secreted from OHO tumor plays a role in osteomalacia. Matrix extracellular phosphoglycoprotein was proposed as a candidate of this phosphaturic factor phosphoglycoprotein (Rowe et. al., *Genomics* (2000) 67:56-68).

Phosphate plays a central role in many of the basic processes essential to the cell and the mineralization of skeleton. In particular, skeletal mineralization is dependent on the regulation of phosphate and calcium in the body and any disturbances in phosphate-calcium homeostasis can have severe repercussions on the integrity of bone. In the kidney, phosphate is lost passively into the glomerular filtrate and is actively reabsorbed via a sodium (Na+) dependent phosphate cotransporter. In the intestine, phosphate is absorbed from foods. A sodium (Na+) dependent phosphate cotransporter was found to be expressed in the intestine and recently cloned (Hilfiker, PNAS 95(24) (1998), 14564-14569). The liver, skin and kidney are involved in the conversion of vitamin D3 to its active metabolite, calcitriol, which plays an active role in the maintenance of phosphate balance and skeletal mineralization.

Vitamin D deficiency causes rickets in children and osteomalacia in adults. Both conditions are characterized by failure of calcification of osteoid, which is the matrix of skeleton.

Thus, all of the humoral functions by matrix extracellular phosphoglycoprotein, namely, renal phosphate leak, hypophosphatemia (low serum phosphate levels), low serum calcitriol (1,25-vitamin D3), are harmful to healthy skeletal formation.

Matrix extracellular phosphoglycoprotein is a large polypeptide with 525 amino acid with short N-terminus signal sequence. Therefore, it is highly probable that this molecule is secreted from its producing cells into the body fluid and circulation. Out of its 525 amino acid sequence, 23 amino acid motif on the C-terminus showed high similarities to a group of bone-tooth mineral matrix phosphoglycoproteins such as osteopontin (OPN), dentin sialophosphoprotein (DSPP), dentin matrix protein 1 (DMP1), and bone sialoprotein II (IBSP). It has been proposed that these bone-tooth mineral matrix phosphoproteins may play important roles in skeletal mineralization.

Notwithstanding the above observations about matrix extracellular phosphoglycoprotein, smaller peptide sequence containing integrin binding motif that is located within the amino acid sequence and far from its C-terminus sequence with a high degree of similarity to other bone-tooth mineral matrix phosphoglycoproteins demonstrated a very potent skeletal formation activity and increased the number of osteoblasts on such skeletal formation surface. The potency of such activities was equivalent to fibroblast growth factor (FGF). It was surprising in that small motifs within a large protein which protein has destructive functions on the skeleton demonstrated potent bone formation activity, and that such motifs were located far from the sequence which showed homology to other known bone-tooth matrix proteins.

Another surprising fact was that potent skeletal formation motifs of the invention contained an integrin binding motif, in particular, RGD sequence. It has been reported that a synthetic peptide containing the RGD sequence inhibited bone formation and resorption in a mineralizing organ culture system of fetal rat skeleton (Gronowicz et. al. Journal of Bone and Mineral Research 9(2):193-201 (1994)), that is a very similar experimental method used to test the subject of the present invention.

Further, the skeletal formation activity provided by the small peptides of the invention was as potent as that of an intact growth factor such as FGF.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Synthesis of D-00001, etc

Six different peptides were manually synthesized by the 9-fluorenylmethoxycarbonyl (Fmoc) strategy and prepared in the C-terminal amide form. The six peptides are as follows:

```
D-00001:  IPSDFEGSGYTDLQE           (SEQ ID NO:41)
D-00002:  DFEGSGYTDLQERGD           (SEQ ID NO:42)
D-00003:  YTDLQERGDNDISPF           (SEQ ID NO:43)
D-00004:  ERGDNDISPFSGDGQ           (SEQ ID NO:44)
D-00005:  NDISPFSGDGQPFKD           (SEQ ID NO:45)
D-00006:  TDLQERGDNDISPFSGDGQPFKD   (SEQ ID NO:46)
(C-terminus amidated)
```

Amino acid derivatives and resins were purchased from Bachem, Inc., Torrance, Calif., and Novabiochem, La Jolla, Calif. The respective amino acids were condensed manually in a stepwise manner using 4-(2',4'-dimethoxyphenyl-Fmoc-aminomethyl)-phenoxy resin. N-methyl pyrrolidone was used during the synthesis as a solvent. For condensation, diisopropylcarbodiimide/N-hydroxybenzotriazole was employed, and for deprotection of $N^\alpha$-Fmoc groups, 20% piperidine in N-methylpyrrolidone was employed. The following side chain protecting groups were used: Asn and Gln, trityl; Asp, Glu, Ser, and Thr, t-butyl; Arg, 2,2,5,7,8-pentamethylchroman-6-sulfonyl; and Lys, t-butoxycarbonyl. Resulting protected peptide resins were deprotected and cleaved from the resin using a trifluoroacetic acid-thioanisole-m-cresol-ethanedithiol-$H_2O$ (80:5:5:5:5, v/v) at 20° C. for 2 h. Resulting crude peptides were precipitated and washed with ethyl ether then purified by reverse-phase high performance liquid chromatography (using Vydac 5C18 column and a gradient of water/acetonitrile containing 0.1% trifluoroacetic acid). All peptides were obtained with 5-20% yield (from the starting resin). Purity of the peptides was confirmed by analytical high performance liquid chromatography. Identity of the peptides was confirmed by a Sciex API IIE triple quadrupole ion spray mass spectrometer.

Example 2

Fetal Mouse Calvarial Assay

Reagents

FGF-1 was purchased from Peprotech Inc. (Rocky Hill, N.J.). RGD-1, 2, 3, 4, 5 and 6 (referred to here as D-00001, D-00002, D-00003, D-00004, D-00005 and D-00006) were provided by Dr. Nomizu (Hokkaido University, Japan).

Mice

Pregnant ICR mice were purchased from SLC Japan Co. Ltd. (Shizuoka, Japan).

Mouse Calvarial Organ Culture

Mouse calvarial organ culture was performed as described in Mundy G et al. *Science* 286: 1946-1949, 1999 and Traisnedes K et al. *Endocrinoloy* 139: 3178-3184, 1998. The calvaria from 4-days-old mice were excised and cut in half along the sagittal suture. Each half of the calvaria was placed on a stainless steel grid in a 12-well tissue culture dish (Asahi Glass Techno Corp., Funabashi, Japan). Each well contained 1.5 ml of BGj medium (Sigma, St. Louis, Mo.) supplemented with 0.1% bovine serum albumin (Sigma) and each compound. FGF-1 was used as a positive control as described by Mundy et al. The medium was changed at day 1 and 4, and the assay was terminated at day 7.

Histomorphometrical Analysis

Calvaria was fixed with 10% neutral-buffered formalin, decalcified with 4.13% EDTA and embedded in paraffin. 4 mm-thickness sections were made and stained with hematoxylin and eosin. New bone area was measured using Inage-Pro Plus (Media Cybernetics, Silver Spring, Md.).

The six peptides of Example 1 were tested for their ability to enhance bone growth with the tests being carried out as described above in Example 2. The peptides which did not include the RGD sequence did not show positive results. The other four peptides showed positive results with the best results being obtained with the sequences D-00004: ERGDNDISPFSGDGQ, (SEQ ID NO:44)
and

D-00006: TDLQERGDNDISPFSGDGQPFKD (SEQ ID NO:46).

The best results are in FIG. 3 (specifically FIGS. 3C and 3D). Data from these results are graphically shown in FIG. 4.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A formulation, comprising: a pharmaceutically acceptable carrier; and an L-conformation peptide contiguous with an RGD sequence of naturally occurring protein matrix extracellular phosphoglycoprotein consisting of 15 to 35 amino acids, wherein the peptide is comprised of an RGD integrin binding motif and wherein the peptide enhances bone growth.

2. A formulation, comprising: a pharmaceutically acceptable carrier; and a peptide chosen from:

| | |
|---|---|
| DFEGSGYTDLQERGD, | (SEQ ID NO:42) |
| YTDLQERGDNDISPF, | (SEQ ID NO:43) |
| ERGDNDISPFSGDGQ, and | (SEQ ID NO:44) |
| TDLQERGDNDISPFSGDGQPFKD. | (SEQ ID NO:46). |

3. A formulation of claim 2, wherein the peptide is

| | |
|---|---|
| TDLQERGDNDISPFSGDGQPFKD | (SEQ ID NO:46). |

* * * * *

SEQUENCE LISTING

```
<160> NUMBER OF SEQ ID NOS: 46

<210> SEQ ID NO 1
<211> LENGTH: 97
<212> TYPE: PRT
<213> ORGANISM: Artificial Sequence
<220> FEATURE:
<223> OTHER INFORMATION: peptide of dental product

<400> SEQUENCE: 1

Asp Ser Gln Ala Gln Lys Ser Pro Val Lys Ser Lys Ser Thr His Arg
1               5                   10                  15

Ile Gln His Asn Ile Asp Tyr Leu Lys His Leu Ser Lys Val Lys Lys
            20                  25                  30

Ile Pro Ser Asp Phe Glu Gly Ser Gly Tyr Thr Asp Leu Gln Glu Arg
        35                  40                  45

Gly Asp Asn Asp Ile Ser Pro Phe Ser Gly Asp Gly Gln Pro Phe Lys
    50                  55                  60

Asp Ile Pro Gly Lys Gly Glu Ala Thr Gly Pro Asp Leu Glu Gly Lys
65                  70                  75                  80

Asp Ile Gln Thr Gly Phe Ala Gly Pro Ser Glu Ala Glu Ser Thr His
                85                  90                  95

Leu

<210> SEQ ID NO 2
<211> LENGTH: 47
<212> TYPE: PRT
<213> ORGANISM: Artificial Sequence
<220> FEATURE:
<223> OTHER INFORMATION: peptide of dental product

<400> SEQUENCE: 2

Ala Gln Lys Ser Pro Val Lys Ser Lys Ser Thr His Arg Ile Gln His
1               5                   10                  15
```

```
Asn Ile Asp Tyr Leu Lys His Leu Ser Lys Val Lys Lys Ile Pro Ser
            20                  25                  30

Asp Phe Glu Gly Ser Gly Tyr Thr Asp Leu Gln Glu Arg Gly Asp
            35                  40                  45

<210> SEQ ID NO 3
<211> LENGTH: 47
<212> TYPE: PRT
<213> ORGANISM: Artificial Sequence
<220> FEATURE:
<223> OTHER INFORMATION: peptide of dental product

<400> SEQUENCE: 3

Arg Gly Asp Ala Gln Lys Ser Pro Val Lys Ser Lys Ser Thr His Arg
 1               5                  10                  15

Ile Gln His Asn Ile Asp Tyr Leu Lys His Leu Ser Lys Val Lys Lys
            20                  25                  30

Ile Pro Ser Asp Phe Glu Gly Ser Gly Tyr Thr Asp Leu Gln Glu
            35                  40                  45

<210> SEQ ID NO 4
<211> LENGTH: 47
<212> TYPE: PRT
<213> ORGANISM: Artificial Sequence
<220> FEATURE:
<223> OTHER INFORMATION: peptide of dental product

<400> SEQUENCE: 4

Asp Ser Gln Ala Gln Lys Ser Pro Val Lys Ser Lys Ser Thr His Arg
 1               5                  10                  15

Ile Gln His Asn Ile Asp Tyr Leu Lys His Leu Ser Lys Val Lys Lys
            20                  25                  30

Ile Pro Ser Asp Phe Glu Gly Ser Gly Tyr Thr Asp Arg Gly Asp
            35                  40                  45

<210> SEQ ID NO 5
<211> LENGTH: 44
<212> TYPE: PRT
<213> ORGANISM: Artificial Sequence
<220> FEATURE:
<223> OTHER INFORMATION: peptide of dental product

<400> SEQUENCE: 5

Arg Gly Asp Ser Pro Val Lys Ser Lys Ser Thr His Arg Ile Gln His
 1               5                  10                  15

Asn Ile Asp Tyr Leu Lys His Leu Ser Lys Val Lys Lys Ile Pro Ser
            20                  25                  30

Asp Phe Glu Gly Ser Gly Tyr Thr Asp Leu Gln Glu
            35                  40

<210> SEQ ID NO 6
<211> LENGTH: 44
<212> TYPE: PRT
<213> ORGANISM: Artificial Sequence
<220> FEATURE:
<223> OTHER INFORMATION: peptide of dental product

<400> SEQUENCE: 6

Asp Ser Gln Ala Gln Lys Ser Pro Val Lys Ser Lys Ser Thr His Arg
 1               5                  10                  15

Ile Gln His Asn Ile Asp Tyr Leu Lys His Leu Ser Lys Val Lys Lys
            20                  25                  30
```

```
Ile Pro Ser Asp Phe Glu Gly Ser Gly Arg Gly Asp
        35                  40
```

<210> SEQ ID NO 7
<211> LENGTH: 37
<212> TYPE: PRT
<213> ORGANISM: Artificial Sequence
<220> FEATURE:
<223> OTHER INFORMATION: peptide of dental product

<400> SEQUENCE: 7

```
Arg Gly Asp Thr His Arg Ile Gln His Asn Ile Asp Tyr Leu Lys His
 1               5                   10                  15

Leu Ser Lys Val Lys Lys Ile Pro Ser Asp Phe Glu Gly Ser Gly Tyr
            20                  25                  30

Thr Asp Leu Gln Glu
        35
```

<210> SEQ ID NO 8
<211> LENGTH: 41
<212> TYPE: PRT
<213> ORGANISM: Artificial Sequence
<220> FEATURE:
<223> OTHER INFORMATION: peptide of dental product

<400> SEQUENCE: 8

```
Asp Ser Gln Ala Gln Lys Ser Pro Val Lys Ser Lys Ser Thr His Arg
 1               5                   10                  15

Ile Gln His Asn Ile Asp Tyr Leu Lys His Leu Ser Lys Val Lys Lys
            20                  25                  30

Ile Pro Ser Asp Phe Glu Arg Gly Asp
        35                  40
```

<210> SEQ ID NO 9
<211> LENGTH: 27
<212> TYPE: PRT
<213> ORGANISM: Artificial Sequence
<220> FEATURE:
<223> OTHER INFORMATION: peptide of dental product

<400> SEQUENCE: 9

```
Arg Gly Asp Leu Lys His Leu Ser Lys Val Lys Lys Ile Pro Ser Asp
 1               5                   10                  15

Phe Glu Gly Ser Gly Tyr Thr Asp Leu Gln Glu
            20                  25
```

<210> SEQ ID NO 10
<211> LENGTH: 38
<212> TYPE: PRT
<213> ORGANISM: Artificial Sequence
<220> FEATURE:
<223> OTHER INFORMATION: peptide of dental product

<400> SEQUENCE: 10

```
Asp Ser Gln Ala Gln Lys Ser Pro Val Lys Ser Lys Ser Thr His Arg
 1               5                   10                  15

Ile Gln His Asn Ile Asp Tyr Leu Lys His Leu Ser Lys Val Lys Lys
            20                  25                  30

Ile Pro Ser Arg Gly Asp
        35
```

<210> SEQ ID NO 11
<211> LENGTH: 24

```
<212> TYPE: PRT
<213> ORGANISM: Artificial Sequence
<220> FEATURE:
<223> OTHER INFORMATION: peptide of dental product

<400> SEQUENCE: 11

Arg Gly Asp Leu Ser Lys Val Lys Lys Ile Pro Ser Asp Phe Glu Gly
 1               5                  10                  15

Ser Gly Tyr Thr Asp Leu Gln Glu
            20

<210> SEQ ID NO 12
<211> LENGTH: 32
<212> TYPE: PRT
<213> ORGANISM: Artificial Sequence
<220> FEATURE:
<223> OTHER INFORMATION: peptide of dental product

<400> SEQUENCE: 12

Asp Ser Gln Ala Gln Lys Ser Pro Val Lys Ser Lys Ser Thr His Arg
 1               5                  10                  15

Ile Gln His Asn Ile Asp Tyr Leu Lys His Leu Ser Lys Arg Gly Asp
            20                  25                  30

<210> SEQ ID NO 13
<211> LENGTH: 21
<212> TYPE: PRT
<213> ORGANISM: Artificial Sequence
<220> FEATURE:
<223> OTHER INFORMATION: peptide of dental product

<400> SEQUENCE: 13

Arg Gly Asp Val Lys Lys Ile Pro Ser Asp Phe Glu Gly Ser Gly Tyr
 1               5                  10                  15

Thr Asp Leu Gln Glu
            20

<210> SEQ ID NO 14
<211> LENGTH: 28
<212> TYPE: PRT
<213> ORGANISM: Artificial Sequence
<220> FEATURE:
<223> OTHER INFORMATION: peptide of dental product

<400> SEQUENCE: 14

Asp Ser Gln Ala Gln Lys Ser Pro Val Lys Ser Lys Ser Thr His Arg
 1               5                  10                  15

Ile Gln His Asn Ile Asp Tyr Leu Lys Arg Gly Asp
            20                  25

<210> SEQ ID NO 15
<211> LENGTH: 18
<212> TYPE: PRT
<213> ORGANISM: Artificial Sequence
<220> FEATURE:
<223> OTHER INFORMATION: peptide of dental product

<400> SEQUENCE: 15

Arg Gly Asp Ile Pro Ser Asp Phe Glu Gly Ser Gly Tyr Thr Asp Leu
 1               5                  10                  15

Gln Glu

<210> SEQ ID NO 16
<211> LENGTH: 25
```

```
<212> TYPE: PRT
<213> ORGANISM: Artificial Sequence
<220> FEATURE:
<223> OTHER INFORMATION: peptide of dental product

<400> SEQUENCE: 16

Asp Ser Gln Ala Gln Lys Ser Pro Val Lys Ser Lys Ser Thr His Arg
 1               5                  10                  15

Ile Gln His Asn Ile Asp Arg Gly Asp
            20                  25

<210> SEQ ID NO 17
<211> LENGTH: 15
<212> TYPE: PRT
<213> ORGANISM: Artificial Sequence
<220> FEATURE:
<223> OTHER INFORMATION: peptide of dental product

<400> SEQUENCE: 17

Arg Gly Asp Asp Phe Glu Gly Ser Gly Tyr Thr Asp Leu Gln Glu
 1               5                  10                  15

<210> SEQ ID NO 18
<211> LENGTH: 19
<212> TYPE: PRT
<213> ORGANISM: Artificial Sequence
<220> FEATURE:
<223> OTHER INFORMATION: peptide of dental product

<400> SEQUENCE: 18

Asp Ser Gln Ala Gln Lys Ser Pro Val Lys Ser Lys Ser Thr His Arg
 1               5                  10                  15

Arg Gly Asp

<210> SEQ ID NO 19
<211> LENGTH: 12
<212> TYPE: PRT
<213> ORGANISM: Artificial Sequence
<220> FEATURE:
<223> OTHER INFORMATION: peptide of dental product

<400> SEQUENCE: 19

Arg Gly Asp Gly Ser Gly Tyr Thr Asp Leu Gln Glu
 1               5                  10

<210> SEQ ID NO 20
<211> LENGTH: 13
<212> TYPE: PRT
<213> ORGANISM: Artificial Sequence
<220> FEATURE:
<223> OTHER INFORMATION: peptide of dental product

<400> SEQUENCE: 20

Asp Ser Gln Ala Gln Lys Ser Pro Val Lys Arg Gly Asp
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: peptide of dental product

<400> SEQUENCE: 21

Arg Gly Asp Gly Tyr Thr Asp Leu Gln Glu
 1               5                  10
```

<210> SEQ ID NO 22
<211> LENGTH: 10
<212> TYPE: PRT
<213> ORGANISM: Artificial Sequence
<220> FEATURE:
<223> OTHER INFORMATION: peptide of dental product

<400> SEQUENCE: 22

Asp Ser Gln Ala Gln Lys Ser Arg Gly Asp
1               5                   10

<210> SEQ ID NO 23
<211> LENGTH: 40
<212> TYPE: PRT
<213> ORGANISM: Artificial Sequence
<220> FEATURE:
<223> OTHER INFORMATION: peptide of dental product

<400> SEQUENCE: 23

Arg Gly Asp Asn Asp Ile Ser Pro Phe Ser Gly Asp Gly Gln Pro Phe
1               5                   10                  15

Lys Asp Ile Pro Gly Lys Gly Glu Ala Thr Gly Pro Asp Leu Glu Gly
            20                  25                  30

Lys Asp Ile Gln Thr Gly Phe Ala
        35                  40

<210> SEQ ID NO 24
<211> LENGTH: 40
<212> TYPE: PRT
<213> ORGANISM: Artificial Sequence
<220> FEATURE:
<223> OTHER INFORMATION: peptide of dental product

<400> SEQUENCE: 24

Asn Asp Ile Arg Gly Asp Ser Pro Phe Ser Gly Asp Gly Gln Pro Phe
1               5                   10                  15

Lys Asp Ile Pro Gly Lys Gly Glu Ala Thr Gly Pro Asp Leu Glu Gly
            20                  25                  30

Lys Asp Ile Gln Thr Gly Phe Ala
        35                  40

<210> SEQ ID NO 25
<211> LENGTH: 35
<212> TYPE: PRT
<213> ORGANISM: Artificial Sequence
<220> FEATURE:
<223> OTHER INFORMATION: peptide of dental product

<400> SEQUENCE: 25

Asn Asp Ile Ser Pro Phe Arg Gly Asp Ser Gly Asp Gly Gln Pro Phe
1               5                   10                  15

Lys Asp Ile Pro Gly Lys Gly Glu Ala Thr Gly Pro Asp Leu Glu Gly
            20                  25                  30

Lys Asp Ile
        35

<210> SEQ ID NO 26
<211> LENGTH: 30
<212> TYPE: PRT
<213> ORGANISM: Artificial Sequence
<220> FEATURE:
<223> OTHER INFORMATION: peptide of dental product

```
<400> SEQUENCE: 26

Asn Asp Ile Ser Pro Phe Ser Gly Asp Arg Gly Asp Gly Gln Pro Phe
  1               5                  10                  15

Lys Asp Ile Pro Gly Lys Gly Glu Ala Thr Gly Pro Asp Leu
             20                  25                  30

<210> SEQ ID NO 27
<211> LENGTH: 45
<212> TYPE: PRT
<213> ORGANISM: Artificial Sequence
<220> FEATURE:
<223> OTHER INFORMATION: peptide of dental product

<400> SEQUENCE: 27

Phe Ser Gly Asp Gly Gln Pro Phe Lys Asp Ile Pro Gly Lys Gly Glu
  1               5                  10                  15

Ala Thr Gly Pro Asp Leu Glu Gly Lys Asp Ile Gln Thr Gly Phe Ala
             20                  25                  30

Gly Pro Ser Glu Ala Glu Ser Arg Gly Asp Thr His Leu
         35                  40                  45

<210> SEQ ID NO 28
<211> LENGTH: 35
<212> TYPE: PRT
<213> ORGANISM: Artificial Sequence
<220> FEATURE:
<223> OTHER INFORMATION: peptide of dental product

<400> SEQUENCE: 28

Ile Pro Gly Lys Gly Glu Ala Thr Gly Pro Asp Leu Glu Gly Lys Asp
  1               5                  10                  15

Ile Gln Thr Gly Phe Ala Gly Pro Ser Glu Arg Gly Asp Ala Glu Ser
             20                  25                  30

Thr His Leu
         35

<210> SEQ ID NO 29
<211> LENGTH: 30
<212> TYPE: PRT
<213> ORGANISM: Artificial Sequence
<220> FEATURE:
<223> OTHER INFORMATION: peptide of dental product

<400> SEQUENCE: 29

Glu Ala Thr Gly Pro Asp Leu Glu Gly Lys Asp Ile Gln Thr Gly Phe
  1               5                  10                  15

Ala Gly Arg Gly Asp Pro Ser Glu Ala Glu Ser Thr His Leu
             20                  25                  30

<210> SEQ ID NO 30
<211> LENGTH: 33
<212> TYPE: PRT
<213> ORGANISM: Artificial Sequence
<220> FEATURE:
<223> OTHER INFORMATION: peptide of dental product

<400> SEQUENCE: 30

Asn Asp Ile Ser Pro Phe Ser Gly Asp Gly Gln Pro Phe Lys Asp Arg
  1               5                  10                  15

Gly Asp Ile Pro Gly Lys Gly Glu Ala Thr Gly Pro Asp Leu Glu Gly
             20                  25                  30

Lys
```

-continued

```
<210> SEQ ID NO 31
<211> LENGTH: 33
<212> TYPE: PRT
<213> ORGANISM: Artificial Sequence
<220> FEATURE:
<223> OTHER INFORMATION: peptide of dental product

<400> SEQUENCE: 31

Gly Lys Gly Glu Ala Thr Gly Pro Asp Leu Glu Gly Lys Asp Ile Arg
 1               5                  10                  15

Gly Asp Gln Thr Gly Phe Ala Gly Pro Ser Glu Ala Glu Ser Thr His
            20                  25                  30

Leu

<210> SEQ ID NO 32
<211> LENGTH: 40
<212> TYPE: PRT
<213> ORGANISM: Artificial Sequence
<220> FEATURE:
<223> OTHER INFORMATION: peptide of dental product

<400> SEQUENCE: 32

Phe Ser Gly Asp Gly Gln Pro Phe Lys Asp Ile Pro Gly Lys Gly Glu
 1               5                  10                  15

Ala Thr Gly Arg Gly Asp Pro Asp Leu Glu Gly Lys Asp Ile Gln Thr
            20                  25                  30

Gly Phe Ala Gly Pro Ser Glu Ala
        35                  40

<210> SEQ ID NO 33
<211> LENGTH: 31
<212> TYPE: PRT
<213> ORGANISM: Artificial Sequence
<220> FEATURE:
<223> OTHER INFORMATION: peptide of dental product

<400> SEQUENCE: 33

Asp Gly Gln Pro Phe Lys Asp Ile Pro Gly Lys Gly Glu Ala Thr Gly
 1               5                  10                  15

Arg Gly Asp Pro Asp Leu Glu Gly Lys Asp Ile Gln Thr Gly Phe
            20                  25                  30

<210> SEQ ID NO 34
<211> LENGTH: 25
<212> TYPE: PRT
<213> ORGANISM: Artificial Sequence
<220> FEATURE:
<223> OTHER INFORMATION: peptide of dental product

<400> SEQUENCE: 34

Pro Phe Lys Asp Ile Pro Gly Lys Gly Glu Ala Thr Gly Arg Gly Asp
 1               5                  10                  15

Pro Asp Leu Glu Gly Lys Asp Ile Gln
            20                  25

<210> SEQ ID NO 35
<211> LENGTH: 28
<212> TYPE: PRT
<213> ORGANISM: Artificial Sequence
<220> FEATURE:
<223> OTHER INFORMATION: peptide of dental product

<400> SEQUENCE: 35
```

Asp Ile Pro Gly Lys Gly Glu Ala Thr Gly Arg Gly Asp Pro Asp Leu
1               5                   10                  15

Glu Gly Lys Asp Ile Gln Thr Gly Phe Ala Gly Pro
            20                  25

<210> SEQ ID NO 36
<211> LENGTH: 31
<212> TYPE: PRT
<213> ORGANISM: Artificial Sequence
<220> FEATURE:
<223> OTHER INFORMATION: peptide of dental product

<400> SEQUENCE: 36

Asp Gly Gln Pro Phe Lys Asp Ile Pro Gly Lys Gly Glu Ala Thr Gly
1               5                   10                  15

Arg Gly Asp Pro Asp Leu Glu Gly Lys Asp Ile Gln Thr Gly Phe
            20                  25                  30

<210> SEQ ID NO 37
<211> LENGTH: 28
<212> TYPE: PRT
<213> ORGANISM: Artificial Sequence
<220> FEATURE:
<223> OTHER INFORMATION: peptide of dental product

<400> SEQUENCE: 37

Gly Lys Gly Glu Ala Thr Gly Arg Gly Asp Pro Asp Leu Glu Gly Lys
1               5                   10                  15

Asp Ile Gln Thr Gly Phe Ala Gly Pro Ser Glu Ala
            20                  25

<210> SEQ ID NO 38
<211> LENGTH: 19
<212> TYPE: PRT
<213> ORGANISM: Artificial Sequence
<220> FEATURE:
<223> OTHER INFORMATION: peptide of dental product

<400> SEQUENCE: 38

Glu Ala Thr Gly Arg Gly Asp Pro Asp Leu Glu Gly Lys Asp Ile Gln
1               5                   10                  15

Thr Gly Phe

<210> SEQ ID NO 39
<211> LENGTH: 13
<212> TYPE: PRT
<213> ORGANISM: Artificial Sequence
<220> FEATURE:
<223> OTHER INFORMATION: peptide of dental product

<400> SEQUENCE: 39

Glu Ala Thr Gly Arg Gly Asp Pro Asp Leu Glu Gly Lys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: peptide of dental product

<400> SEQUENCE: 40

Glu Ala Thr Gly Arg Gly Asp Pro Asp Leu
1               5                   10

```
<210> SEQ ID NO 41
<211> LENGTH: 15
<212> TYPE: PRT
<213> ORGANISM: Artificial Sequence
<220> FEATURE:
<223> OTHER INFORMATION: D-00001
<220> FEATURE:
<221> NAME/KEY: AMIDATION
<222> LOCATION: 15

<400> SEQUENCE: 41

Ile Pro Ser Asp Phe Glu Gly Ser Gly Tyr Thr Asp Leu Gln Glu
 1               5                  10                  15

<210> SEQ ID NO 42
<211> LENGTH: 15
<212> TYPE: PRT
<213> ORGANISM: Artificial Sequence
<220> FEATURE:
<223> OTHER INFORMATION: D-00002
<220> FEATURE:
<221> NAME/KEY: AMIDATION
<222> LOCATION: 15

<400> SEQUENCE: 42

Asp Phe Glu Gly Ser Gly Tyr Thr Asp Leu Gln Glu Arg Gly Asp
 1               5                  10                  15

<210> SEQ ID NO 43
<211> LENGTH: 15
<212> TYPE: PRT
<213> ORGANISM: Artificial Sequence
<220> FEATURE:
<223> OTHER INFORMATION: D-00003
<220> FEATURE:
<221> NAME/KEY: AMIDATION
<222> LOCATION: 15

<400> SEQUENCE: 43

Tyr Thr Asp Leu Gln Glu Arg Gly Asp Asn Asp Ile Ser Pro Phe
 1               5                  10                  15

<210> SEQ ID NO 44
<211> LENGTH: 15
<212> TYPE: PRT
<213> ORGANISM: Artificial Sequence
<220> FEATURE:
<223> OTHER INFORMATION: D-00004
<220> FEATURE:
<221> NAME/KEY: AMIDATION
<222> LOCATION: 15

<400> SEQUENCE: 44

Glu Arg Gly Asp Asn Asp Ile Ser Pro Phe Ser Gly Asp Gly Gln
 1               5                  10                  15

<210> SEQ ID NO 45
<211> LENGTH: 15
<212> TYPE: PRT
<213> ORGANISM: Artificial Sequence
<220> FEATURE:
<223> OTHER INFORMATION: D-00005
<220> FEATURE:
<221> NAME/KEY: AMIDATION
<222> LOCATION: 15

<400> SEQUENCE: 45

Asn Asp Ile Ser Pro Phe Ser Gly Asp Gly Gln Pro Phe Lys Asp
```

```
                    -continued
1            5            10             15

<210> SEQ ID NO 46
<211> LENGTH: 23
<212> TYPE: PRT
<213> ORGANISM: Artificial Sequence
<220> FEATURE:
<223> OTHER INFORMATION: D-00006
<220> FEATURE:
<221> NAME/KEY: AMIDATION
<222> LOCATION: 23

<400> SEQUENCE: 46

Thr Asp Leu Gln Glu Arg Gly Asp Asn Asp Ile Ser Pro Phe Ser Gly
 1               5                  10                  15

Asp Gly Gln Pro Phe Lys Asp
            20
```